(12) United States Patent
Horiuchi

(10) Patent No.: US 11,216,171 B2
(45) Date of Patent: Jan. 4, 2022

(54) MEDICAL IMAGE MANAGEMENT APPARATUS AND RECORDING MEDIUM

(71) Applicant: Konica Minolta, Inc., Tokyo (JP)

(72) Inventor: Makoto Horiuchi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/871,244

(22) Filed: May 11, 2020

(65) Prior Publication Data

US 2020/0379620 A1  Dec. 3, 2020

(30) Foreign Application Priority Data

May 30, 2019 (JP) .............................. JP2019-101132

(51) Int. Cl.
*G06F 3/0485* (2013.01)
*A61B 5/00* (2006.01)

(52) U.S. Cl.
CPC ............ *G06F 3/0485* (2013.01); *A61B 5/743* (2013.01); *A61B 5/7435* (2013.01); *A61B 5/7445* (2013.01)

(58) Field of Classification Search
CPC ... G06F 3/0485; A61B 5/7445; A61B 5/7435; A61B 5/743
See application file for complete search history.

(56) References Cited

U.S. PATENT DOCUMENTS

| | | | | |
|---|---|---|---|---|
| 6,026,377 A * | 2/2000 | Burke | ................. | G06Q 10/087 235/383 |
| 8,233,037 B2 * | 7/2012 | Matsui | ................. | A61B 1/0005 348/65 |
| 8,777,856 B2 * | 7/2014 | Stuebe | ................. | G16H 50/30 600/437 |
| 9,933,849 B2 * | 4/2018 | Rezaee | ................. | G06F 3/14 |
| 2004/0151358 A1 * | 8/2004 | Yanagita | ................. | G16H 30/40 382/132 |
| 2005/0107690 A1 * | 5/2005 | Soejima | ................. | G06F 19/321 600/425 |
| 2007/0012881 A1 * | 1/2007 | Bartsch | ................. | G16H 50/50 250/363.04 |
| 2007/0106633 A1 * | 5/2007 | Reiner | ................. | G16H 30/20 |
| 2009/0076853 A1 * | 3/2009 | Sagawa | ................. | G16H 30/20 705/3 |
| 2010/0053213 A1 * | 3/2010 | Ishida | ................. | G16H 30/40 345/629 |
| 2010/0256991 A1 * | 10/2010 | Ishikawa | ................. | G06F 19/00 705/3 |

(Continued)

FOREIGN PATENT DOCUMENTS

JP 2012065735 * 5/2012 ............... A61B 8/00
JP 5615113 B2 10/2014

*Primary Examiner* — Phenuel S Salomon
(74) *Attorney, Agent, or Firm* — Lucas & Mercanti, LLP

(57) ABSTRACT

Provided is a medical image management apparatus including a hardware processor that records, when an image interpretation report on a plurality of medical images obtained in a single examination is created, a display time for which each of the plurality of images is displayed during creation of the image interpretation report, and controls, when the plurality of medical images in the single examination is viewed, a viewing speed of each of the plurality of medical images based on the recorded display time of each of the plurality of images during creation of the image interpretation report.

9 Claims, 7 Drawing Sheets

(56) References Cited

U.S. PATENT DOCUMENTS

| | | | |
|---|---|---|---|
| 2013/0229503 A1* | 9/2013 | Taniguchi | G16H 30/40 348/65 |
| 2014/0044421 A1* | 2/2014 | Sasaki | G11B 27/28 386/343 |
| 2014/0072192 A1* | 3/2014 | Reiner | G06F 19/321 382/128 |
| 2015/0262014 A1* | 9/2015 | Iwamura | G16H 50/20 382/128 |
| 2017/0069084 A1* | 3/2017 | Kubo | G06K 9/6267 |
| 2017/0262584 A1* | 9/2017 | Gallix | G16H 30/20 |
| 2018/0325356 A1* | 11/2018 | Tateshita | A61B 1/04 |
| 2018/0350460 A1* | 12/2018 | Hisano | G16H 30/40 |
| 2019/0279408 A1* | 9/2019 | Hirakawa | G06K 9/00469 |
| 2019/0295248 A1* | 9/2019 | Nakamura | G16H 30/40 |
| 2019/0304594 A1* | 10/2019 | Fuchigami | G16H 30/40 |
| 2020/0065614 A1* | 2/2020 | Nishimura | G06K 9/6223 |
| 2020/0253565 A1* | 8/2020 | Nakamura | A61B 5/742 |
| 2020/0258641 A1* | 8/2020 | Nakamura | G16H 50/20 |
| 2020/0379620 A1* | 12/2020 | Horiuchi | A61B 5/7435 |
| 2021/0012870 A1* | 1/2021 | Hirakawa | G16H 30/40 |

\* cited by examiner

| Viewing Cloud | | |
|---|---|---|
| PATIENT EXAMINATION INFORMATION | | 0000557141 |

532a {
PATIENT NAME: JOHN GREEN
PATIENT ID: 0000557141
DATE OF BIRTH: 05/06/1985
AGE: 33
SEX: M
FIRST NAME:
LAST NAME:
ALLERGY HISTORY:
HEIGHT:
WEIGHT:

532b {
RECEPTION NUMBER: 211391101
EXAMINATION ID: 000000000001
EXAMINATION DATE: 02/12/2004
EXAMINATION TIME: 23:19:21
REPORT CREATED BY DR.: JANE JONES
DATE AND TIME: 03/04/2019 11:28:03
REPORT APPROVED BY DR.:
DATE AND TIME:
AGE AS OF DATE OF EXAMINATION: 33
MODALITY: CT
REGION: ABDOMEN
TECHNICIAN: MICHAEL WALTER
REQUESTED BY DR.: RACHEL LEE
EXAMINATION DESCRIPTION: Abdomen^01_abd_8mm ......
IMAGE INTERPRETATION PURPOSE: ......
EXAMINATION PURPOSE: ......

USER NAME: SE KM

532c REPORT HISTORY
532 EXAMINATION ▼1 | MODALITY | REGION | REPORT(S)
532d (scrollbar area)
REFERENCE REPORT(S): NONE CREATE REPORT | APPROVE | TEMPORARILY SAVE | 532f REQUEST APPROVAL | DELETE
IMAGE INTERPRETATION IN PROGRESS REPORT
532e Compared to the last CT scanning (8.19.2008).
Irregularities on liver surface, left lobe outer area, ...

Increment of viable HCC of S4 ...
Liver chirrhosis ...

Increase in density at right lung apex; malignant tumor denied, ...

REFERENCE IMAGE(S)

MEDICAL IMAGE MANAGEMENT APPARATUS AND RECORDING MEDIUM

CROSS-REFERENCE TO RELATED APPLICATIONS

The entire disclosure of Japanese Patent Application No. 2019-101132 filed on May 30, 2019 is incorporated herein by reference in its entirety.

BACKGROUND

Technological Field

The present invention relates to a medical image management apparatus and a recording medium.

Description of the Related Art

In recent years, digitization has been progressing in the medical fields, and medical images, image interpretation reports, etc. are managed as digital data. Doctors interprets a medical image(s) to create an image interpretation report while the medical image(s) are displayed on a display device.

In recent years, modalities have obtained higher performance, and the number of images to be obtained in a single examination has been increasing. For example, in a computed tomography (CT).

Diagnosticians (diagnostic radiologists, doctors who interpret medical images) observe all the images by viewing the obtained frame images one after another with a mouse operation or playing them with a function of "cine play." To make a diagnosis in a limited time, the medical images need to be interpreted in a good balance of time. To that end, the doctors take time to carefully observe an image(s) of a region pointed out or a region with abnormality or suspected abnormality according to an examination order while fast-forwarding the rest.

For example, JP5615113B2 discloses a technique that involves: in response to a user setting out a range of images to be successively displayed as a movie from multiple images for which image interpretation report information is input, generating an input screen for inputting image interpretation report information for the group of images in the set image range; continuously displaying the movie of the set range of images up until the end of input of the image interpretation report; and generating combined data in which each of the group of images is associated to the input image interpretation report information and storing the generated data in a memory.

SUMMARY

In the technique of JP5615113B2, the group of images used during input of the image interpretation report is stored with the image interpretation report associated thereto. Thus, in a case where the group of images for which an image interpretation report has been created is reinterpreted for follow-up observation, etc., the group of images in the image range used during input of the image interpretation report, and the other images are to be excluded from the target of reinterpretation. However, even if the diagnostician who has created an image interpretation report reinterprets the medical images himself, it seems difficult to remember which image in the range of images was focused on for interpretation in the past. If the medical images are reinterpreted by another diagnostician than the previous time, it is impossible to know which image in the range of images was focused on by the diagnostician who previously interpreted the medical images unless a message or the like is attached. Thus, the medical images cannot be efficiently reinterpreted.

An object of the present invention is to make it possible to effectively reinterpret multiple medical images taken in an examination.

To achieve at least one of the abovementioned objects, a medical image management apparatus reflecting one aspect of the present invention includes a hardware processor that:

records, when an image interpretation report on a plurality of medical images obtained in a single examination is created, a display time for which each of the plurality of images is displayed during creation of the image interpretation report; and controls, when the plurality of medical images in the single examination is viewed, a viewing speed of each of the plurality of medical images based on the recorded display time of each of the plurality of images during creation of the image interpretation report.

To achieve at least one of the abovementioned objects, a recording medium reflecting another aspect of the present invention stores a computer-readable program that causes a computer:

to record, when an image interpretation report on a plurality of medical images obtained in a single examination is created, a display time for which each of the plurality of images is displayed during creation of the image interpretation report; and to control, when the plurality of medical images in the single examination is viewed, a viewing speed of each of the plurality of medical images based on the recorded display time of each of the plurality of images during creation of the image interpretation report.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein:

FIG. 5 shows an example of an image interpretation screen to be displayed at Step S7 in FIG. 4;

FIG. 6 shows an example of the image interpretation report creation screen; and

DETAILED DESCRIPTION OF THE EMBODIMENTS

Hereinafter described is an embodiment of a medical image management apparatus according to the present invention. However, the scope of the present invention is not limited to the embodiments or illustrated examples.

Figure 1:
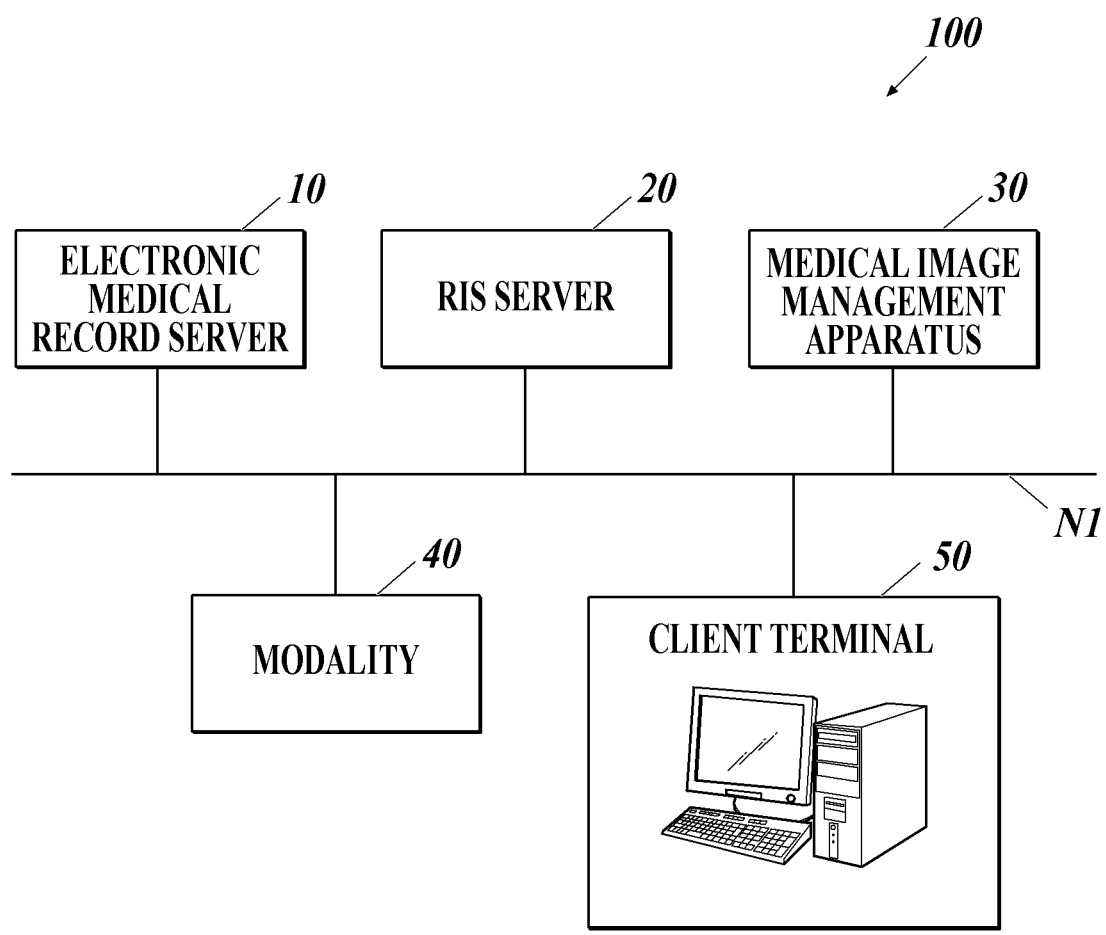
FIG. 1 shows a system configuration of a medical image system in an embodiment.

FIG. 1 shows a system configuration of a medical image system 100 in this embodiment. As shown in FIG. 1, the medical image system 100 includes an electronic medical record server 10, a radiological information system (RIS) server 20, a medical image management apparatus 30, a modality 40, and a client terminal 50. The components of the medical image system 100 are connected to one another via a facility network N1 such as a local area network (LAN) for data communication. The components are in conformity with HL7 (Health Level Seven) and DICOM (Digital Image and Communications in Medicine) standard and communicate with one another in conformity with HL7 and DICOM.

The electronic medical record server 10 generates information on clinical records of a medical practice, diagnosis, etc. on a patient and an examination order for requesting an examination of a patient according to an operation command by the client terminal 50.

The examination order includes a name of a doctor who requested the examination (attending doctor), a name of a diagnostician, patient information, examination information, etc.

The patient information is information on the patient. The patient information includes a patient ID, patient name, date of birth, age, sex, height, weight, blood pressure (systolic/diastolic), blood type, body temperature, history of present illness, past medical history, inpatient/outpatient classification, allergy record, infection record, etc.

The examination record includes information on the examination. The examination information includes an examination ID, examination date, modality (DR, CR, US, CT, MRI, etc.), examined region (chest, abdomen, etc.), technician name, medical department, examination purpose, image interpretation purpose, use or non-use of contrast agent, reception number, etc.

The examination purpose is information from the personnel who requested the examination for informing the examination technician or the diagnostician of the purpose of the examination.

The image interpretation purpose is information from the personnel who requested the examination for informing the diagnostician of the purpose or the points of the image interpretation.

The RIS server 20 manages the information in the radiology department such as reservations of examination or treatment using the radiological apparatuses and examination results. The RIS server 20 manages an examination order(s) issued in the electronic medical record server 10. The RIS server 20 then sends an examination request to the modality 40 to be used for the examination and sends an image reading request to the medical image management apparatus 30.

The medical image management apparatus 30 stores therein image data of the medical image generated in the modality 40 and manages the data for each patient. The medical image management apparatus 30 may be a PACS (Picture Archiving and Communication System), for example.

Figure 2:
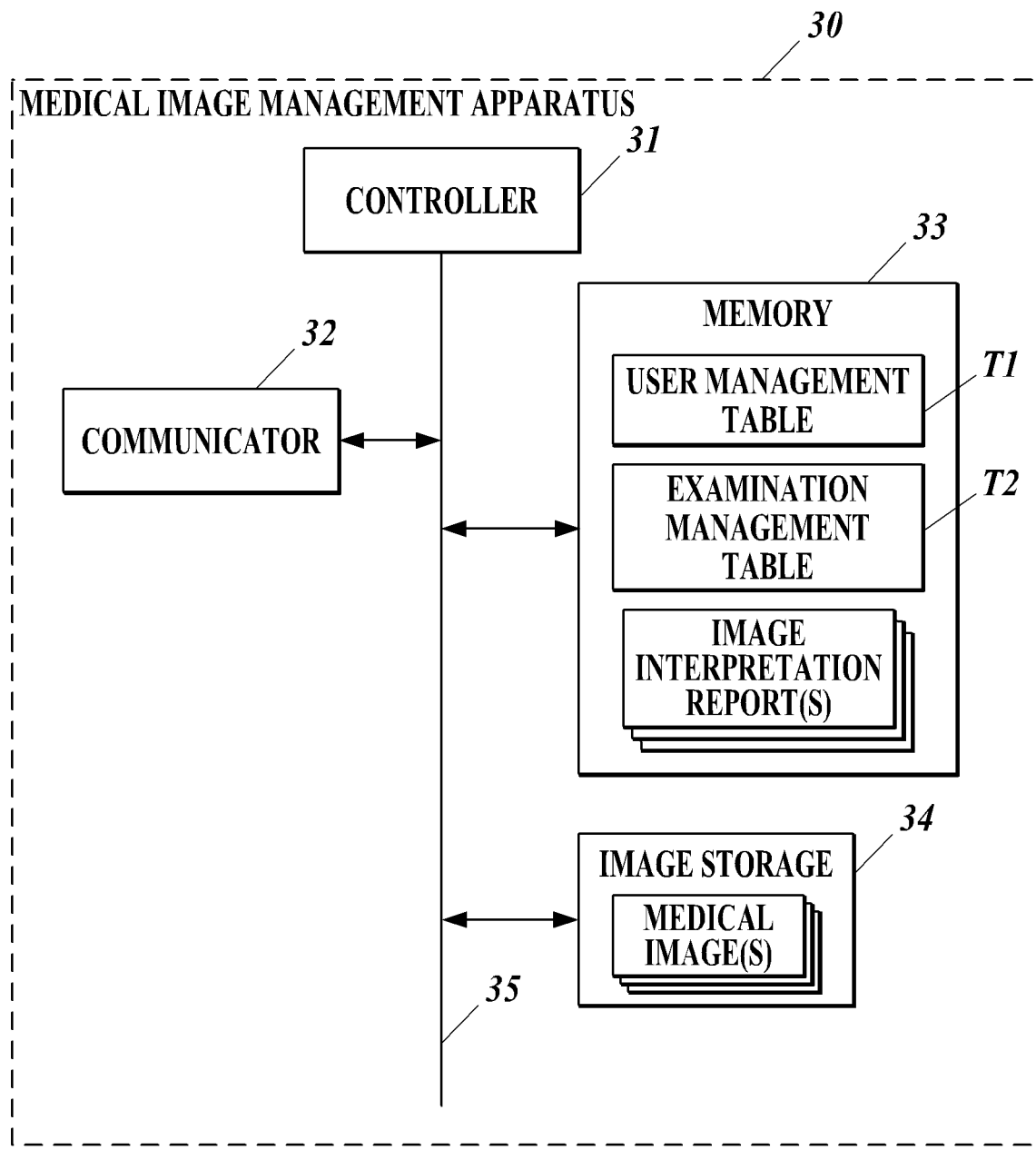
FIG. 2 shows a functional configuration of a medical image management apparatus.

FIG. 2 shows a functional configuration of the medical image management apparatus 30.

As shown in FIG. 2, the medical image management apparatus 30 includes a controller (hardware processor) 31, a communicator 32, a memory 33, and an image storage 34, which are connected to one another by a bus 35.

The controller 31 includes a central processing unit (CPU), a read only memory (ROM), and a random access memory (RAM), and centrally controls processing operations of the components of the medical image management apparatus 30. Specifically, the CPU reads out various processing programs stored in the ROM and develops them in the RAM to perform the various kinds of processing in cooperation with the programs. A web server program, an application program, etc. are stored in the ROM. The web server program imparts to a web server a function of offering various web screens for a web browser installed on the client terminal 50 by communication with the web browser over the HTTP protocol. The application program operates on the web server for providing information on medical images to the user of the client terminal 50 via the web browser.

The communicator 32 includes a network interface and sends and receives data to and from an external device(s) connected via the facility network N1.

The memory 33 includes a hard disk and a non-volatile memory, and stores therein various kinds of data. For example, a user management table T1, and an examination management table T2, and an image interpretation report(s) are stored in the memory 33.

The user management table T1 is for managing users of the image management system provided by the medical image management apparatus 30. A user ID, password, name, where the user belongs (medical facility, department), e-mail address, etc. are saved in the user management table T1, associated to each user (medical staff).

The examination management table T2 is for managing imaging examinations. A name of a personnel who requested examination (attending doctor), name of diagnostician, patient information, examination information, identification information of medical image(s) (image ID), identification information of image interpretation report(s) (report ID), etc. are saved in the examination management table T2, associated to each imaging examination. For example, in a case where multiple medical images at different slice positions (different positions in the body-axis direction) are generated in a single examination by CT or MRI, an image ID and a slice number (assigned in the order of slice positions) are associated to each medical image to be saved.

The image interpretation report is a report on an image diagnosis which is created according to an operation command from the client terminal 50 when the diagnostician interprets a medical image on the client terminal 50. The image interpretation report is identified by the report ID.

The image storage 34 is for storing and preserving the image data of medical images of each patient. Each medical image is identified with the image ID.

The modality 40 is an image generator such as an X-ray imaging apparatus (DR, CR), an ultrasound diagnostic apparatus (US), a CT scanner, and an MRI scanner, and generates medical images by imaging the patient. The modality 40 writes the associated information (patient information, image ID, slice number, etc.) onto the header of the image file of the medical image(s) in conformity with the DICOM standards, and associates the associated information to the medical image(s).

The client terminal 50 is a computer device such as a PC, tablet terminal, and smartphone used by a doctor. The attending doctor creates an electronic medical record, generates an examination order, and views medical images and image interpretation reports on the client terminal 50. The diagnostician interprets medical images and creates image interpretation reports on the client terminal 50.

Figure 3:
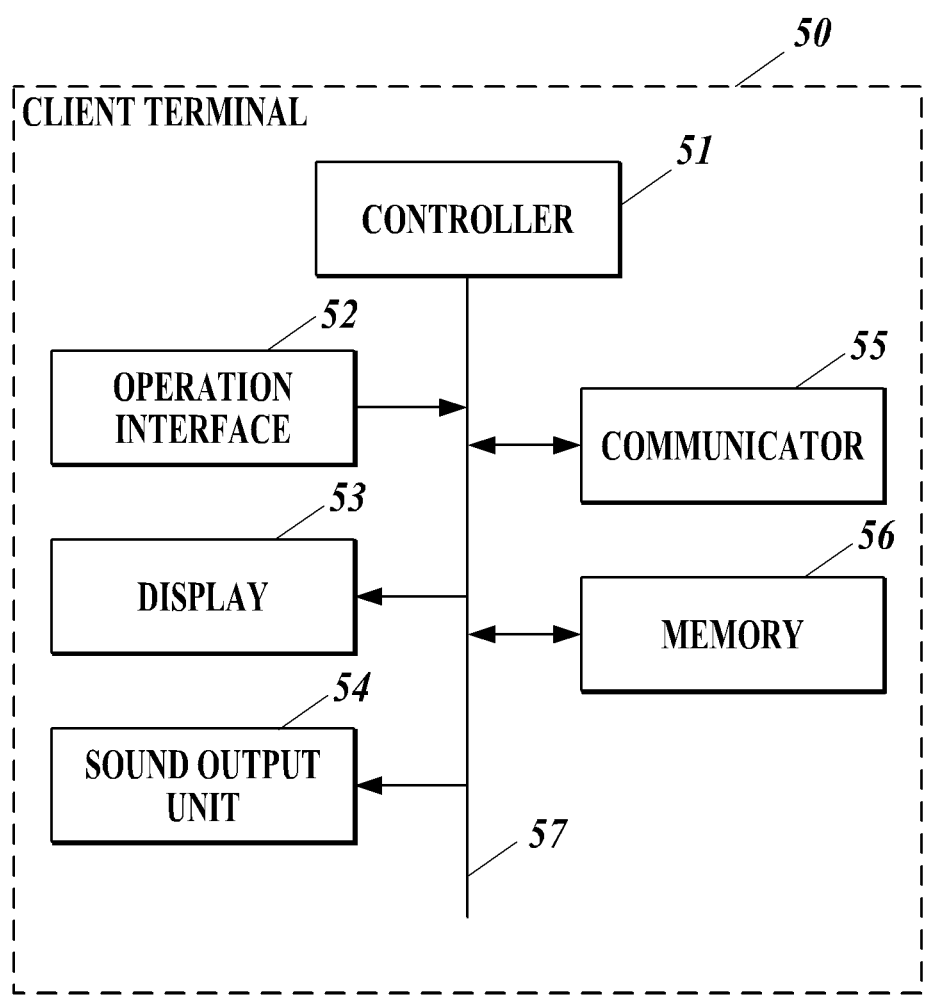
FIG. 3 shows a functional configuration of a client terminal.

FIG. 3 shows a functional configuration of the client terminal 50.

As shown in FIG. 3, the client terminal 50 includes a controller (hardware processor) 51, an operation interface 52, a display 53, an audio output unit 54, a communicator 55, and a memory 56, which are connected with one another by a bus 57.

The controller 51 includes a CPU, ROM, and ROM, and centrally controls the processing operations of the components of the client terminal 50. Specifically, the CPU reads out various processing programs stored in the ROM and develops them in the RAM to perform the various kinds of processing in cooperation of the programs. A web browser program for realizing web browser, etc. are stored in the ROM.

The operation interface 52 includes a keyboard with cursor keys, character and number input keys, function keys, etc. and a pointing device such as a mouse, and outputs, to the controller 51, operation signals input by key operation on the keyboard or mouse operation. The operation interface 52 with a touch panel overlaid on the display 53 outputs, to the controller 51, operation signals according to the positions of touch operation by the user's finger, etc.

The display 53 includes a monitor such as a liquid crystal display (LCD), and various screens are displayed thereon according to the command of display signals input from the controller 51. The display 53 may include a single monitor or multiple monitors.

The audio output unit 54 includes a speaker and a D/A conversion circuit. The audio output unit 54 converts digital signals into analog signals based on the audio data, and outputs sounds from the speaker on the basis of the analog signals.

The communicator 55 includes a network interface and sends and receives data to and from an external device(s) connected via the facility network N1.

The memory 56 includes a hard disk and a non-volatile semiconductor memory, and stores therein various kinds of data.

Next, the operation of the medical image system 100 is described.

Figure 4:
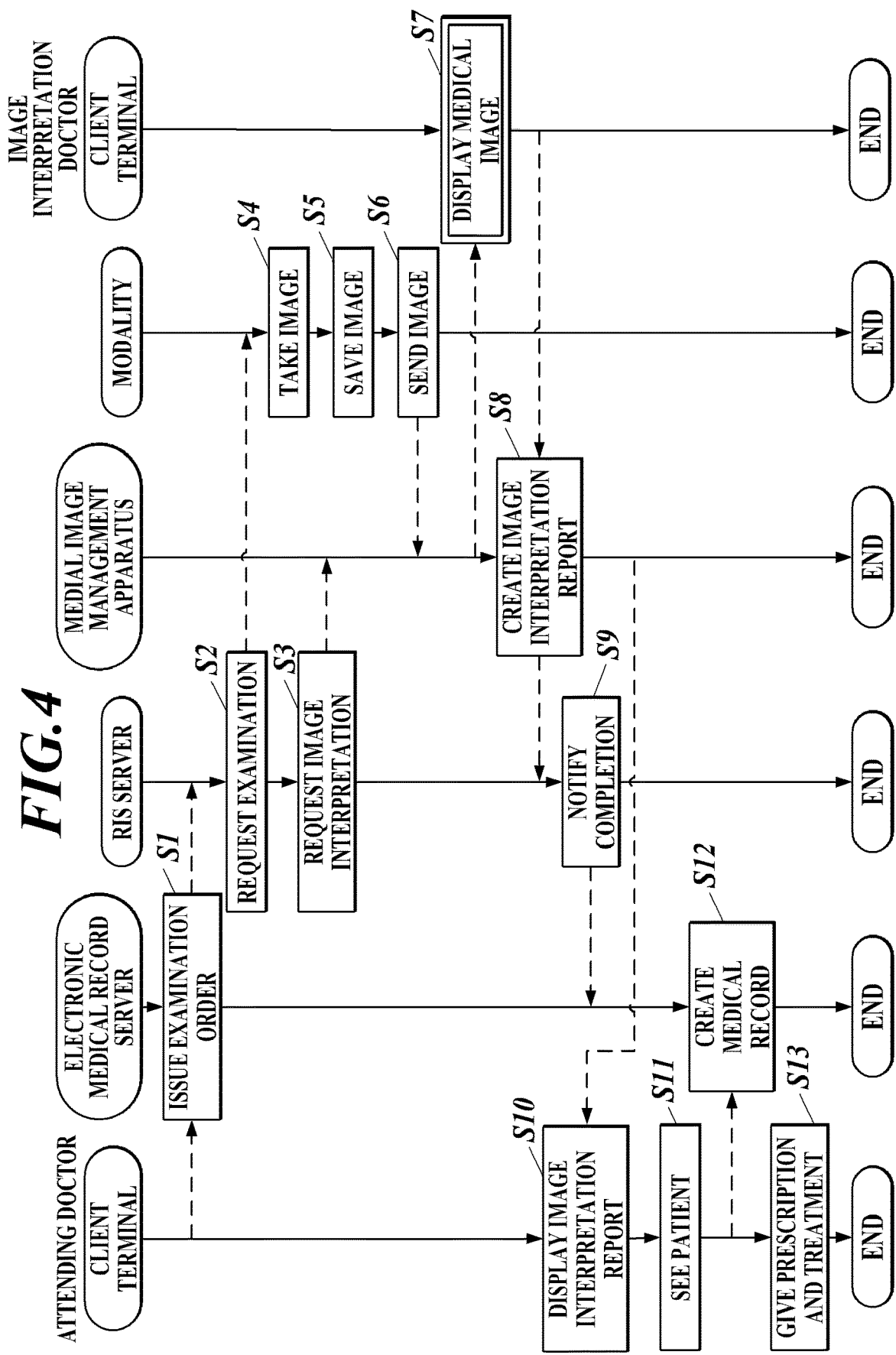
FIG. 4 is a ladder chart showing a usual workflow in the medical image system.

FIG. 4 is a ladder chart showing a usual workflow in the medical image system 100.

First, the attending doctor gets access to the electronic medical record server 10 from the client terminal 50, specifies a patient, examination details, etc., and issues an examination order (Step S1). The electronic medical record server 10 then sends the examination order to the RIS server 20.

The RIS server 20 sends an examination request to the modality 40 on the basis of the examination order received from the electronic medical record server 10 (Step S2). The RIS server 20 then sends an image interpretation request to the medical image management apparatus 30 (Step S3). The examination request and the image interpretation request may include any selected part of the information included in the examination order. The examination order itself may be sent from the RIS server 20 to the modality 40 or the medical image management apparatus 30.

The modality 40 receives the examination request from RIS server 20 and takes an image(s) of a target region of a target patient according to the operation of the examination technician on the basis of the examination request (Step S4), and saves the medical image generated (Step S5). The modality 40 sends the medical image generated in the examination to the medical image management apparatus 30 (Step S6).

When the medical image management apparatus 30 receives the medical image(s) the modality 40, the controller 31 specifies the image interpretation request corresponding to the medical image(s) out of the image interpretation requests received from the RIS server 20 on the basis of the associated information of the medical image(s), and saves the medical image(s) and the specified image interpretation request (patient information, examination information, etc.) which are associated to one another. Specifically, the controller 31 stores the medical image(s) in the image storage 34, and saves the personnel who requested the examination, the diagnostician, the patient information, the examination information, the image ID and the slice number of the medical image(s) in the examination management table T2 in the memory 33.

When the diagnostician gets access to the medical image management apparatus 30 via the client terminal 50 and selects the examination which is the target of medical image interpretation via the operation interface 52, the controller 31 of the medical image management apparatus 30 shows the medical image(s) of the selected examination on the display 53 of the client terminal 50 (Step S7).

The diagnostician interprets the medical image(s) displayed on the display 53 of the client terminal 50, inputs the interpretation results via the operation interface 52, and creates an image interpretation report (Step S8). The created image interpretation report is sent to the medical image management apparatus 30 by the communicator 55. In the medical image management apparatus 30, the controller 31 manages the created image interpretation report associating to the patient information and the examination information. Specifically, the controller 31 stores the image interpretation report in the memory 33 and saves the report ID of the image interpretation report in the record of the concerning examination in the examination management table T2. In the examination management table T2, as a name of the personnel who requested examination, name of the diagnostician, patient information, examination information, image ID of medical image(s), report ID of image interpretation report(s), etc. are associated to one another, the medical image(s) and the image interpretation report created for the concerning medical image(s) are associated to each other.

Next, the medical image management apparatus 30 sends to the RIS server 20 a notification of completion of image interpretation, and the RIS server 20 then sends to the electronic medical record server 10 a notification of completion of image interpretation (Step S9).

When the attending doctor gets access to the medical image management apparatus 30 via the client terminal 50, the image interpretation report is displayed on the display 53 of the client terminal 50 (Step S10).

The attending doctor sees the patient (Step S11), gets access to the electronic medical record server 10 via the client terminal 50, and creates an electronic medical record (Step S12). Specifically, the attending doctor makes a treatment plan with reference to the image interpretation report, and explains it to the patient. The attending doctor gives prescription and treatment to the patient (Step S13).

Hereinafter, the displaying of the medical image(s) at Step S7 and the creation of the image interpretation report at Step S8 are described in detail.

Figure 5:
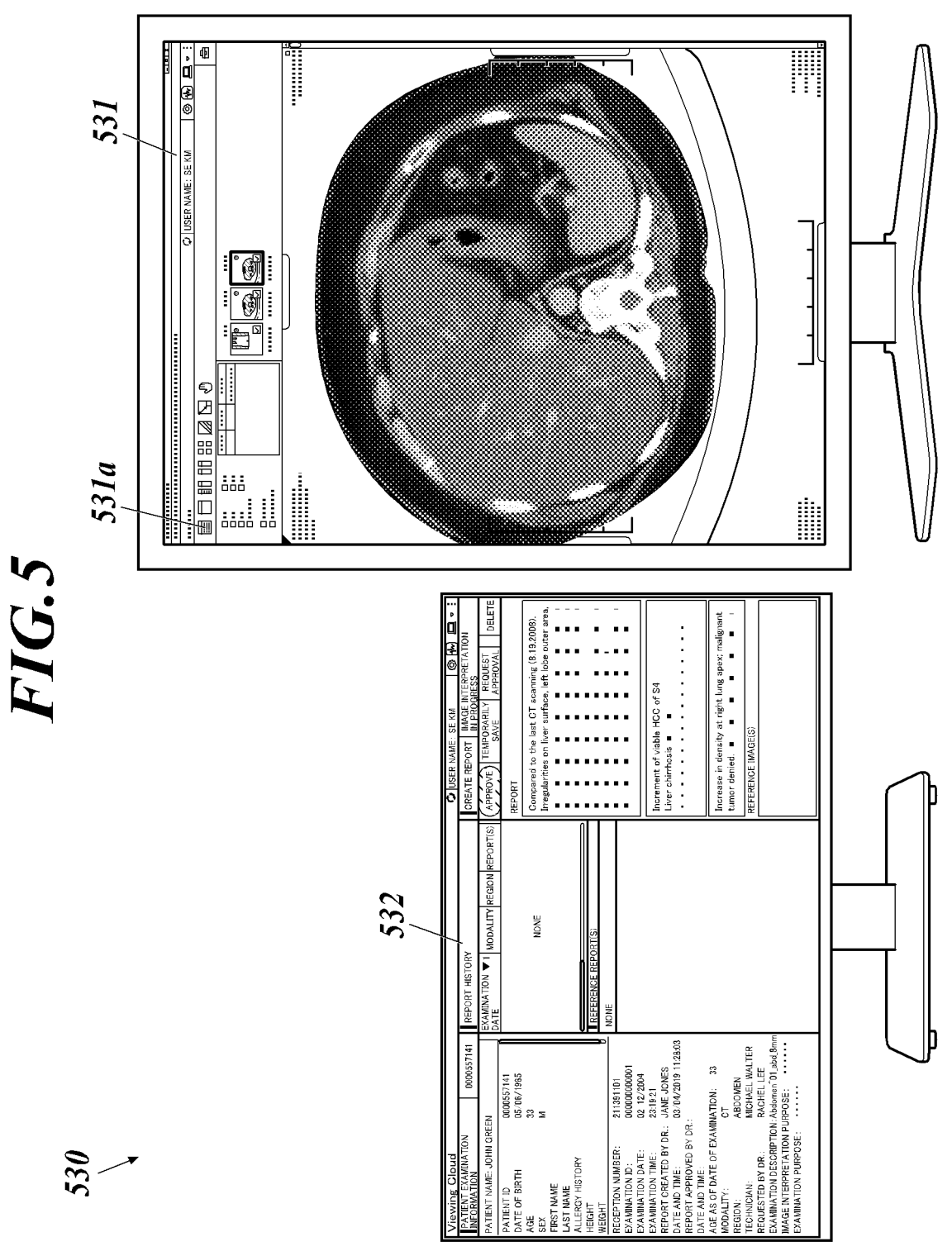

FIG. 5 shows an example of an image interpretation screen 530 to be displayed on the display 53 by the medical image management apparatus 30 at Step S7. The image interpretation screen 530 includes an image display screen 531 and an image interpretation report creation screen 532. In FIG. 5, the display 53 has two monitors on which the image display screen 531 and the image interpretation report creation screen 532 are respectively displayed. However, the image display screen 531 and the image interpretation report creation screen 532 may be displayed together on one monitor, or may be split on three or more monitors. The image interpretation screen 530 is a web-based screen, and the operation of the image interpretation screen 530 via the operation interface 52 is sent to the medical image management apparatus 30 by the communicator 55, and the controller 31 of the medical image management apparatus 30 executes processing and display control according to the operation by the diagnostician on the image interpretation screen 530.

The medical image(s) in a selected examination are displayed on the image display screen 531. In a case where the selected examination is CT, MRI, or the like, and involves multiple medical images, the diagnostician interprets the medical images while switching the medical images to be displayed in an order (of slice numbers) by the image switching operation using a mouse wheel, etc. of the operation interface 52. The screen display screen 531 includes a list button 531a. The diagnostician may press the list button 531a via the operation interface 52 to display a list, and select another examination (for example, medical image(s) of an examination in the past in which the same region of the same patient is imaged) to be displayed on the image display screen 531 from the list.

As shown in FIG. 6, the image interpretation report creation screen 532 includes a patient information display area 532a, an examination information display area 532b, a past report display area 532c, a reference report display area 532d, a report input area 532e, and an approval request button 532f. The patient information corresponding to the medical image(s) displayed on the image display screen 531 is displayed in the patient information display area 532a.

The examination information corresponding to the medical image(s) displayed on the image display screen 531 is displayed in the examination information display area 532b. A list of the image interpretation reports on the examinations of the concerning patient in the past is displayed in the past report display area 532c. When a past report is selected on the list via the operation interface 52, the selected past report is displayed, for example, on a pop-up screen. The report input area 532e is a field where the diagnostician inputs an image interpretation report. The approval request button 532f is a button for requesting a doctor in charge for an approval of an image interpretation report.

The diagnostician interprets the medical image(s) displayed on the image display screen 531 according to the image interpretation purpose or the examination purpose displayed in the examination information display area 532b, for example. In a case where the purpose of image interpretation is follow-up observation or where there is an image interpretation report(s) in the past examination(s), the diagnostician may sometimes create an image interpretation report on the newly taken medical image(s) while reinterpreting the medical image(s) in the past examination(s) which are displayed (viewed) on the image display screen 531 by the operation via the operation interface 52. In a case where the past examination involves multiple medical images, an automatic view button is displayed together, and the multiple medical images in the past examination are successively displayed in an order in response to the automatic view button being pressed via the operation interface 52.

In a case where the past examination to be interpreted includes a lot of medical images of CT and MRI, it takes much time and effort to find an important medical image(s) to which the diagnostician gave attention among the medical images. It is common to add an annotation to a point of focus in the medical image(s), for example, so as to make it possible to find the important medical image(s) by using such an annotation. However it takes time and effort to find the important image(s) out of a lot of images. The important medical image(s) may sometimes be overlooked in a case where annotations are added to multiple medical images. In a case where the important medical image(s) is marked as a key image(s), it is possible to immediately read out and interpret the important medical image(s). However, in a case where there are multiple key images, it is difficult to tell which key image is more important. It is also difficult to interpret the medical images from an overall perspective by, for example, viewing the previous and next images of the key image.

When the diagnostician creates an image interpretation report on an examination in which multiple medical images were taken, he/she displays a medical image(s) including a point of focus from the multiple medical images and creates the image interpretation report by observing the displayed medical image(s). That is, a medical image that displayed for a longer time when creating an image interpretation report is more important.

In view of this, in this embodiment, the display time of each medical image during creation of an image interpretation report is recorded, and when a group of medical images in the past examination is viewed, each medical image is displayed at a viewing speed corresponding to the display time recorded for the concerning medical image.

Figure 7:
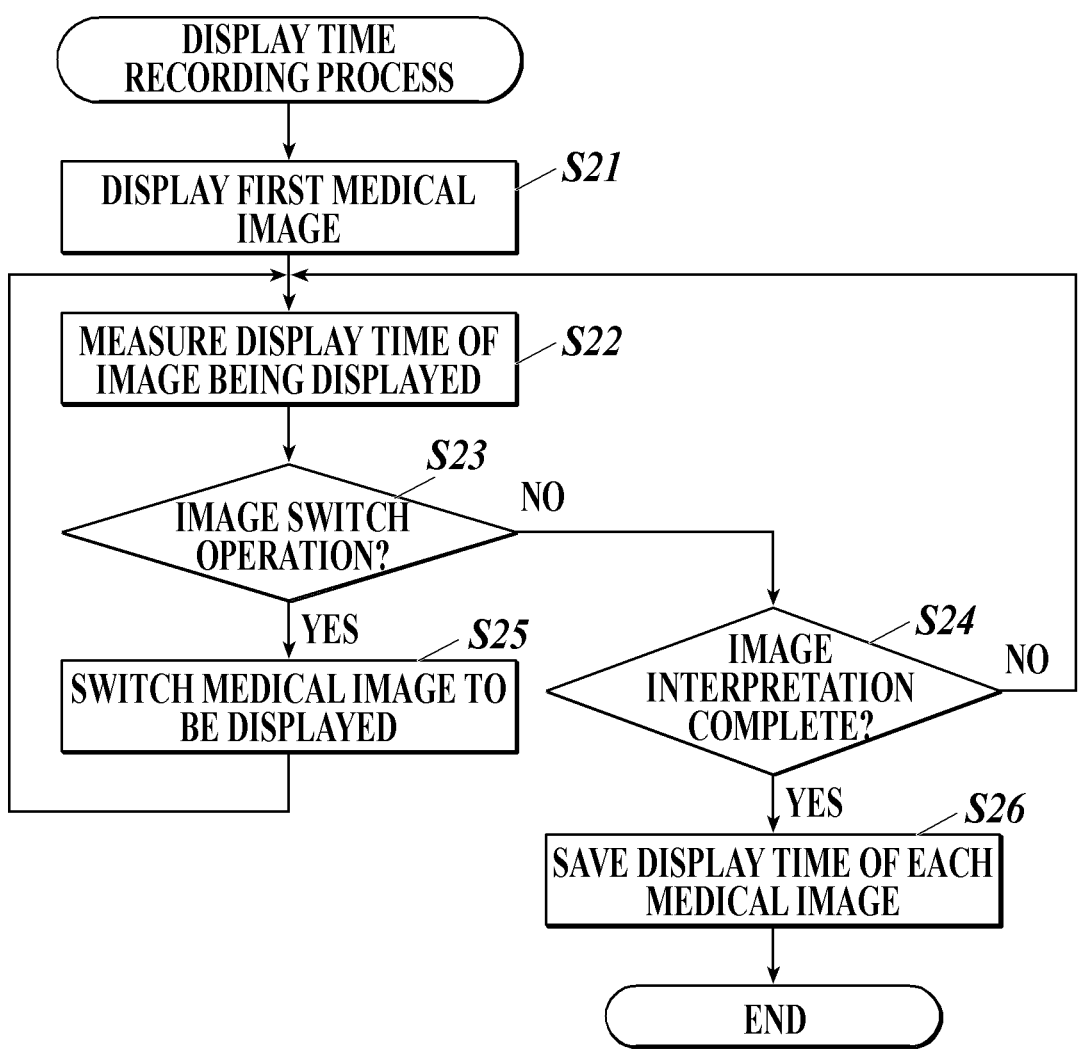
FIG. 7 is a flowchart showing a display time recording process executed by a controller of the medical image management apparatus.

FIG. 7 is a flowchart showing a display time recording process executed by the controller 31 of the medical image management apparatus 30 when an examination using a modality in which multiple medical images are taken in each imaging (for example, CT, MRI, and US) is selected as a target of the image report creation via the operation interface 52 in the client terminal 50. The display time recording process is executed in cooperation of the controller 31 and the programs stored in the memory 33.

First, the first medical image is displayed on the display 53 of the client terminal 50 by the controller 31 (Step S21), and the display time of the medical image being displayed is measured by the controller 31 (Step S22). For example, a counter area associated to the image ID of each medical image of the target examination is provided, and the value of the counter area associated to the medical image currently displayed is incremented at predetermined time intervals by the controller 31.

Next, the controller 31 determines whether or not an image switching operation is performed via the operation interface 52 (Step S23).

If the image switching operation is not performed via the operation interface 52 (Step S23; NO), the controller 31 determines whether or not the image interpretation is finished (Step S24). Whether or not the image interpretation is finished can be determined based on whether or not the approval request button 532f is pressed on the image interpretation report creation screen 532, for example.

If the image interpretation is not finished (Step S24; NO), the controller 31 returns the process to Step S22.

If the image switching operation is performed via the operation interface 52 at Step S23 (Step S23; YES), the controller 31 switches the medical images to be displayed on the image display screen 531 according to the image switching operation (Step S25). The controller 31 then returns the process to Step S22. That is, the display time of the medical image being displayed is incremented.

The controller 31 repeatedly executes the process at Steps S22 to S25, and if the image interpretation is finished (Step S24; YES), the controller 31 stores the display time of each medical image in the examination management table T2, associated to the image ID. The controller 31 then ends the display time recording process.

The image interpretation report created on the image interpretation report creation screen 532 is stored in the memory 33 of the medical image management apparatus 30.

As described above, the diagnostician displays and observes a medical image(s) with a point of focus when creating an image interpretation report. Thus, a medical image displayed for a longer time when creating an image interpretation report is more important. In the display time recording process, the display time of each medical image when creating an image interpretation report is automatically recorded. Thus, the record about which medical image is more important is kept while the diagnostician interprets medical images and creates an image interpretation report as usual without adding an annotation deliberately. Further, the weighting, which shows the importance, can be automatically added to each medical image.

When an automatic view of a group of medical images of a past examination is requested in the client terminal 50, the controller 31 of the medical image management apparatus 30 reads out the display time of each medical image of the past examination, which was recorded in the image interpretation report creation, from the examination management table T2, and shows the medical images in an order (of slice numbers) while controlling the speed on the basis of the display times of the medical images.

The controller 31 may have a predetermined functional equation F denoting a decrease in the viewing speed v (slower speed) for an increase in the display time t, obtains the viewing speed vn of each medical image by substituting the display time to of each medical image n (n=1, 2, 3, . . . ) in the functional equation F, and exerts control so that the medical image n is played at the obtained viewing speed vn, for example. This makes the more important medical image (s) to which an attention was given to be displayed slower, the diagnostician who reinterprets the medical images can intuitively understand which medical image is the important medical image(s) that required time for another diagnostician to make an interpretation when he/she created the image interpretation report in the past even if no handover is done between them. This enables effective reinterpretation of the medical images.

Alternatively, for example, a user interface that allows the user to set different viewing speeds may be provided in the image display screen 531, and the controller 31 may select, according to the display time of each medical image, one of the viewing speeds set by the user. Also in such a case, a slower viewing speed is selected for a longer display time. For example, in a case where the viewing speed is set by three steps, a viewing speed v1 is set for medical images having a display time of a predetermined threshold value TH1 or less, a viewing speed v2 for those having a display time of greater than the predetermined threshold value TH1 and a predetermined threshold value TH2 or less, and a viewing speed v3 for those having a display time of greater than the predetermined threshold value TH2 (TH1<TH2, v1>v2>v3). Also in such a case, the diagnostician who reinterprets the medical images can intuitively understand which medical image is the important medical image(s) on which more time was spent for interpretation thereof. This enables effective reinterpretation of the medical images. The viewing speed is different between diagnosticians because of different levels of skill. Thus, a suitable display of the medical images can be achieved as the users can freely select the viewing speed.

However, in a case where one medical image among multiple medical images was given attention to (displayed) in creation of an image interpretation report, the diagnostician who reinterprets the medical images cannot observe the medical images before and after the one important medical image, just with the one important medical image being viewed slowly.

Thus, the controller 31 may specify the medical image(s) which has a display time in creation of the image interpretation report of greater than a predetermined threshold value, and exert control so that the viewing speed of the specified medical image(s) and the surrounding medical images thereof in a predetermined range is slower than that of the other medical images. The viewing speed of the specified medical image and the medical images within the predetermined range from the specified image can be set by the user on the image display screen 531. The viewing speed of the medical images in the predetermined range may be constant, or alternatively, may be varied according to the distance from the specified medical image. For example, a medical image nearer to the specified medical image may have a slower viewing speed. In a case where multiple medical images are specified and there is a medical image(s) included in the predetermined ranges concerning two or more specified medical images, multiple viewing speeds may be applied for the same medical image(s). In such a case, a slower viewing speed of the set viewing speeds may be set forth, for example.

As described hereinbefore, the controller 31 of the medical image management apparatus 30 records the display time of each medical image during creation of an image interpretation report on multiple medical images obtained in one examination, and controls the viewing speed on the basis of the display time of each medical image during creation of the image interpretation report when the multiple medical images of the examination are viewed.

In that way, the diagnostician who reinterprets the medical images can intuitively understand which medical image is the important medical image(s) on which more time was spent for interpretation thereof. This enables effective reinterpretation of the medical images.

For example, the controller 31 exerts control so that the viewing speed of the medical image displayed for a longer time in creation of the image interpretation report is slower. Thus, the diagnostician who reinterprets the medical images can observe a more important medical image more carefully.

The controller 31 selects one of predetermined viewing speeds for each of the medical images according to the display time so as to control the viewing speeds of the medical images, for example. Thus, the viewing speed is prevented from being slower than necessary, and each medical image can be viewed at an appropriate speed according to the display time.

Alternatively, a user interface that allows the user to set different viewing speeds may be provided, and the controller 31 may select, according to the display time of each medical image, one of the viewing speeds set beforehand by the user, for example. In that way, the medical images can be displayed at a speed suitable for the user.

The controller 31 specifies the medical image(s) having a display time during creation of the image interpretation report of greater than a predetermined threshold value, and exerts control so that the viewing speed of the specified medical image(s) and the medical images within a predetermined range from the specified image is slower than that of the other medical images, for example. Thus, even in the case where one medical image is given attention to during creation of the image interpretation report, the diagnostician who reinterprets the medical images can take some time to observe the surrounding medical images before and after the one important medical image.

The above description for the embodiments merely illustrates examples of the medical image management apparatus according to the present invention, and the present invention is not limited thereto.

For example, in the above description, the medical image management apparatus 30 has a function as a server and executes the display time recording process, etc. in response to the operation on the client terminal 50. However, the medical image management apparatus 30 may include an operation interface and a display, and executes the display time recording process according to the operation on an image interpretation screen on the display of the medical image management apparatus 30 itself.

Furthermore, although in the above description, a ROM is used as a computer-readable recording medium storing the program(s) for executing the processes, the computer-readable recording medium is not limited thereto. As the computer-readable recording medium, a nonvolatile memory, such as a flash memory, and a portable recording medium, such as a CD-ROM, may also be used. Further, as a medium to provide data of the programs of the present invention, a carrier wave can be used.

As for the other detailed configurations and the detailed operations of devices forming the medical image system, modifications can be made as needed within the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A medical image management apparatus comprising a hardware processor that:
   shows a plurality of medical images generated by a modality on the basis of a single examination request to a user on a client terminal for creating an image interpretation report on the plurality of medical images, the plurality of medical images being shown to the user one at a time based on user input;
   records, when the image interpretation report on the plurality of medical images obtained in the single examination is created, a display time for which each of the plurality of images is shown to the user on the client terminal during creation of the image interpretation report; and
   controls, when an automatic view of the plurality of medical images is requested after the image interpretation report is created, a viewing speed of each of the plurality of medical images based on the recorded display time of each of the plurality of images during creation of the image interpretation report.

2. The medical image management apparatus according to claim 1,
   wherein the hardware processor executes the control so that the viewing speed is slower for a medical image having a longer display time and so that the viewing speed is faster for a medical image having a shorter display time.

3. The medical image management apparatus according to claim 1,
   wherein the hardware processor selects, for each of the plurality of medical images, the viewing speed from a preset plurality of predetermined viewing speeds according to the display time so as to control the viewing speed of each of the plurality of medical images.

4. The medical image management apparatus according to claim 3, comprising a setting unit that allows a user to set the plurality of viewing speeds,
   wherein the hardware processor selects, for each of the plurality of medical images, the viewing speed from the plurality of viewing speeds preset by the user according to the display time.

5. The medical image management apparatus according to claim 1,
   wherein the hardware processor specifies a medical image having a recorded display time during the creation of the image interpretation report of greater than a predetermined threshold value, and executes control so that the specified medical image and medical images within a predetermined range in a viewing order from the specified medical image are displayed at a viewing speed slower than a viewing speed of the other medical images.

6. A non-transitory recording medium storing a computer-readable program that causes a computer:
   to show a plurality of medical images generated by a modality on the basis of a single examination request to a user on a client terminal for creating an image interpretation report on the plurality of medical images, the plurality of medical images being shown to the user one at a time based on user input;
   to record, when the image interpretation report on the plurality of medical images obtained in a single examination is created, a display time for which each of the plurality of images is shown to the user on the client terminal during creation of the image interpretation report; and
   to control, when an automatic view of the plurality of medical images is requested after the image interpretation report is created, a viewing speed of each of the plurality of medical images based on the recorded display time of each of the plurality of images during creation of the image interpretation report.

7. The medical image management apparatus according to claim 1, wherein the view of the plurality of medical images is an automatic view in which the plurality of medical images are successively displayed and the viewing speed of each of the plurality of medical images during the automatic view is controlled based on the recorded display time of each of the plurality of images during creation of the image interpretation report, the viewing speed being related to a time of display of the each of the plurality of medical images during the automatic view.

8. A medical image management apparatus comprising a hardware processor that:
   records, when an image interpretation report on a plurality of medical images obtained in a single examination is created, a display time for which each of the plurality of images is displayed during creation of the image interpretation report; and
   when an automatic view of the plurality of medical images in the single examination is requested after the image interpretation report is created, shows the plurality of medical images in succession and controls a viewing speed of each of the plurality of medical images during the automatic view based on the recorded display time of the each of the plurality of images during creation of the image interpretation report.

9. The medical image management apparatus according to claim 8,
wherein the hardware processor executes the control so that the viewing speed is slower for a medical image having a longer display time and so that the viewing speed is faster for a medical image having a shorter display time.

* * * * *